(12) United States Patent
Zeeuw et al.

(10) Patent No.: US 9,102,586 B2
(45) Date of Patent: Aug. 11, 2015

(54) METHOD FOR PRODUCING DADPM (71) Applicant: Huntsman International LLC, The Woodlands, TX (US)

(72) Inventors: Arend-Jan Zeeuw, Overijse (BE); Mark Geoffrey Bent, Voorburg (NL)

(73) Assignee: Huntsman International LLC, The Woodlands, TX (US)

( * ) Notice: Subject to any disclaimer, the term of this patent is extended or adjusted under 35 U.S.C. 154(b) by 0 days.

(21) Appl. No.: 14/159,875

(22) Filed: Jan. 21, 2014

(65) Prior Publication Data
US 2014/0135528 A1 May 15, 2014

Related U.S. Application Data (62) Division of application No. 13/376,632, filed as application No. PCT/EP2010/057049 on May 21, 2010, now Pat. No. 8,697,913.

(30) Foreign Application Priority Data

Jun. 17, 2009 (EP) .................................... 09162887

(51) Int. Cl.
| | |
|---|---|
| *C07C 211/00* | (2006.01) |
| *C07C 209/00* | (2006.01) |
| *C07C 209/68* | (2006.01) |
| *C07C 209/36* | (2006.01) |
| *C07C 209/78* | (2006.01) |

(Continued)

(52) U.S. Cl.
CPC ............. *C07C 209/68* (2013.01); *C07C 201/08* (2013.01); *C07C 209/36* (2013.01); *C07C 209/78* (2013.01); *C07C 209/82* (2013.01); *C02F 1/20* (2013.01); *C02F 9/00* (2013.01); *C02F 2101/322* (2013.01); *C02F 2101/38* (2013.01)

(58) Field of Classification Search
CPC combination set(s) only.
See application file for complete search history.

(56) References Cited

U.S. PATENT DOCUMENTS

| 3,625,886 A | 12/1971 | Mattia |
| 4,994,242 A | 2/1991 | Rae et al. |

(Continued)

FOREIGN PATENT DOCUMENTS

| DE | 10 2006 008 000 | 11/2006 |
| EP | 0 436 443 | 7/1991 |

(Continued)

OTHER PUBLICATIONS

International Search Report and Written Opinion regarding corresponding application No. PCT/EP2010/057049 dated Oct. 6, 2010.

*Primary Examiner* — Clinton Brooks
(74) *Attorney, Agent, or Firm* — Robert A. Diaz (57) ABSTRACT According to the present invention, a method of producing DADPM is provided. The method comprises: converting benzene into nitrobenzene thereby providing a nitrobenzene stream and a first aqueous waste stream comprising nitrobenzene; converting said nitrobenzene from said nitrobenzene stream into aniline, thereby providing an aniline stream and a first part of a second aqueous waste stream comprising aniline; removing nitrobenzene from said aniline prior to converting said aniline from said aniline stream into DADPM; converting said aniline from said aniline stream into DADPM thereby providing a second part of said second aqueous waste stream comprising aniline; stripping aniline and nitrobenzene from said first and second aqueous waste stream by means of a stripping column; providing the stripped aniline and nitrobenzene to said aniline cleaning apparatus or to said nitrobenzene stream.

5 Claims, 2 Drawing Sheets (51) Int. Cl.
 *C07C 201/08* (2006.01)
 *C07C 209/82* (2006.01)
 *C02F 1/20* (2006.01)
 *C02F 9/00* (2006.01)
 *C02F 101/32* (2006.01)
 *C02F 101/38* (2006.01)

(56) References Cited

U.S. PATENT DOCUMENTS

| | | |
|---|---|---|
| 5,313,009 A | 5/1994 | Guenkel et al. |
| 5,963,878 A | 10/1999 | Brereton et al. |
| 6,288,289 B1 | 9/2001 | Boyd et al. |
| 8,557,949 B2 | 10/2013 | Carr et al. |
| 2005/0224424 A1 | 10/2005 | Knauf et al. |
| 2007/0203364 A1 | 8/2007 | Dugal et al. |

FOREIGN PATENT DOCUMENTS

| | | |
|---|---|---|
| EP | 0 489 211 | 6/1992 |
| EP | 0 976 718 | 2/2000 |
| EP | 1 484 312 | 12/2004 |
| EP | 0 711 6768 | 9/2007 |
| WO | 2009/037088 | 3/2009 |

METHOD FOR PRODUCING DADPM

CROSS-REFERENCE TO RELATED APPLICATIONS

This application is a divisional of U.S. patent application Ser. No. 13/376,632, pending, which is the National Phase of International Application PCT/EP10/57049 filed May 21, 2010 which designated the U.S. and which claims priority to EP Application No. 09162887.5 filed Jun. 17, 2009. The noted applications are incorporated herein by reference.

The present invention relates to a chemical installation for providing DADPM, more particular to an integrated chemical installation comprising a nitrobenzene production unit for converting benzene into nitrobenzene, an aniline production unit for converting nitrobenzene into aniline and a DADPM (being diaminodiphenylmethane) production unit for converting the aniline into DADPM, optionally completed with an MDI unit for converting the DADPM to MDI (diphenylmethane diisocyanate).

The present invention further relates to a production process for producing DADPM and optionally for producing MDI.

Chemical installations for providing DADPM (also referred to as MDA) are known in the art. Diaminodiphenylmethane, and more in general methylene-bridged polyphenyl polyamines, are typically prepared from aniline, or from aniline derivatives, by reacting them with formaldehyde in the presence of a solution of a strong acid such as, for example, hydrochloric, sulfuric or phosphoric acid. Literary sources which describe this type of synthesis are: J. Am. Chem. Soc. 57, 888, 1975; Chem. Tech., November 1984, 670; Kirk Othmer, Vol. II, $3^{rd}$ Edition, 338-348. Some other catalysts, such as diatomaceous earth, clay or zeolites were suggested to be used in the conversion of aniline and formaldehyde to DADPM.

After the conversion of aniline and formaldehyde (typically supplied and used as formalin), the DADPM is present in a reactor effluent stream comprising said DADPM, aniline, acid (used as catalyst), water and some other compounds present as impurities in the supply streams or obtained by side reactions. Since typically hydrochloric acid is used as catalyst, and because this acid is neutralized after the reaction using a base, typically caustic soda, the effluent stream is a salty stream.

The DADPM is separated from the effluent stream by means of a phase separator. The aqueous effluent of this first phase separator, often referred to as brine, is washed with aniline to remove the traces of DADPM still present in this aqueous effluent. The resulting streams are an aqueous phase, comprising water and aniline, separated from an organic phase, being aniline and the traces of DADPM.

In the aqueous stream or brine, aniline is present. To remove as much aniline from this aqueous stream, and to provide an aqueous, optionally salty, stream suitable to be treated in biological waste stream treatment installations, the aniline is stripped from the aqueous stream using a stripping column, often referred to as aniline stripper, amine brine stripper, or amine water stripper.

The aniline used in the DADPM production unit typically is provided as a bulk chemical. Aniline itself is provided in an aniline production unit, often located remote from the DADPM production unit. The conversion of nitrobenzene into aniline also generates an aqueous waste stream comprising water and aniline, which is to be cleaned from aniline and thereafter to be treated in a biochemical treatment unit.

Because the aniline used in DADPM production is to be free of nitrobenzene, the aniline production unit often comprises an aniline cleaning apparatus for removing nitrobenzene from the aniline produced.

An example of a process to clean crude aniline is disclosed in US2007/0203364A1.

The nitrobenzene used in the aniline production unit is typically provided as a bulk chemical as well. This nitrobenzene production unit generates, next to nitrobenzene, an aqueous waste stream in which nitrobenzene is present. Also this waste stream is to be cleaned from nitrobenzene and thereafter to be treated in a biochemical treatment unit. An example of a process to provide nitrated aromatic hydrocarbons is disclosed in EP1484312A1.

US2005/0224424A1 discloses a method to clean crude nitrobenzene.

When all three units are present one near the other, i.e. the nitrobenzene production unit, the aniline production unit and the DADPM production unit, and optionally completed with an MDI production unit for converting the DADPM into MDI, it is clear that some economical and technical benefit can be obtained by feeding all waste streams to be treated into one and the same biological waste water treating unit. Large scale benefits for this biological waste water treatment unit are obtained, and only one unit is to be financed, monitored, controlled and maintained.

However there is still the disadvantage that the organic compound, either aniline or nitrobenzene, is to be removed from each individual waste stream prior to feeding an aqueous streams to the biological waste water treatment unit.

Surprisingly it was found that there is a way to combine the aqueous waste streams prior to removal of the organic components (be it aniline or nitrobenzene), clean out the organic compounds in a way sufficient to provide one aqueous stream of biological treatable waste water, and in the meantime allow recycling the aniline, and optionally the nitrobenzene, to the production cycle of production of DADPM.

The above objective is accomplished by a chemical installation according to the present invention.

According to a first aspect of the present invention, a chemical installation is provided. The chemical installation comprises
  A first unit for providing a first aqueous waste stream comprising nitrobenzene;
  At least a second unit for providing a second aqueous waste stream comprising aniline.

The chemical installation comprises an aniline cleaning apparatus for removing nitrobenzene from aniline, and further comprises a stripping column for stripping aniline from an aqueous stream. The first and second aqueous waste stream are provided to the stripping column, stripping aniline and nitrobenzene from the first and the aqueous waste stream, and the stripped aniline and nitrobenzene is provided to the aniline cleaning apparatus.

According to some embodiments, in the chemical installation,
  the first unit may be a nitrobenzene production unit for converting benzene into nitrobenzene thereby providing a nitrobenzene stream and the first aqueous waste stream comprising nitrobenzene; and
  the second unit may be an aniline production unit for converting the nitrobenzene from the nitrobenzene stream into aniline, thereby providing an aniline stream and the second aqueous waste stream or a first part of the second aqueous waste stream comprising aniline.

The installation further may comprise a DADPM production unit for converting the aniline from the aniline stream into DADPM thereby providing a second part of the second aqueous waste stream comprising aniline.

The first aqueous waste stream comprising nitrobenzene may be the aqueous effluent of a phase separator, separating the produced nitrobenzene from the typically acid water. This water entered in the nitrobenzene production unit along with the acids used in the process (sulphuric acid, nitric acid) or is obtained as reaction water produced during the conversion the first aqueous waste stream may be the aqueous phase of the phase separator, comprising the acids used in the nitrobenzene production, water, some nitrobenzene (typically less than 0,5 wt %, such as less than or equal to 0,3 wt %) and some nitrophenols, nitrates and nitrites (all typically at ppm-level). This aqueous phase may be neutralized using a base, preferably caustic soda. As such, the aqueous stream may comprise salts, optionally sodium salts, of sulphuric acid and nitric acid.

The second aqueous waste stream may be provided by different units, each unit providing part of the second aqueous waste stream.

The first part of this second aqueous waste stream comprising aniline may be the effluent of the aniline reactor. Nitrobenzene and hydrogen are reacted forming aniline and water.

The outlet stream of the reactor is cooled and then phase separated by gravity. The aqueous phase of this phase separation hence comprises water (typically 95,95 wt %) and some aniline (typically about 4,04 wt %).

The second part of this second aqueous waste stream comprising aniline may be the aqueous effluent of a phase separator, separating aniline (as organic phase) from the aqueous stream obtained during DADPM production, typically after washing the water or brine with this aniline. The second part of this second aqueous waste stream comprises water (typically about 81,08 wt %), the salt of the acid catalyst (typically 16,55 wt %), hence typically being sodium chloride, aniline (typically about 1,71 wt %), and other components at ppm-levels.

The parts of the second aqueous waste stream may be mixed, either partially or completely, prior to feeding it into the stripping column, or in the alternative, may be provided to the stripping column as individual streams.

According to the present invention, any number of aqueous waste streams comprising nitrobenzene and/or aniline could be handled as long as the nitrobenzene and/or aniline levels in the water/brine are below the solubility limit, as is typically the case if you carry out a phase separation correctly.

Optionally the chemical installation has an aniline production unit which comprises a reactor for converting said nitrobenzene into aniline, the aniline cleaning apparatus for removing nitrobenzene from the provided aniline being coupled to and fed with the effluent of this reactor. This aniline cleaning apparatus is also referred to as aniline polisher.

The stripped aniline and nitrobenzene may be provided to an aniline cleaning apparatus by feeding the stripped aniline and nitrobenzene together with the aniline from the reactor, or by feeding the stripped aniline and nitrobenzene along with the nitrobenzene to the reactor, which on its turn may convert a part or all of the stripped nitrobenzene into aniline before the stripped aniline is fed to the aniline cleaning apparatus.

According to some embodiments of the present invention, the aniline production unit may comprise a reactor for converting the nitrobenzene into aniline, the aniline cleaning apparatus for removing nitrobenzene from the provided aniline may be coupled to the effluent of the reactor, and the stripped aniline and nitrobenzene may be provided to said reactor for converting said nitrobenzene into aniline.

According to some embodiments of the present invention, the aniline production unit may comprise a reactor for converting the nitrobenzene into aniline, the aniline cleaning apparatus for removing nitrobenzene from the provided aniline being coupled to the effluent of said reactor, the stripped aniline and nitrobenzene being provided the effluent of this reactor prior to the aniline cleaning apparatus.

This has the advantage that the nitrobenzene cannot influence the DADPM production in the DADPM production unit situated downstream this aniline cleaning apparatus.

The aniline stripper separates the aqueous waste stream, according to the invention comprising the first and second waste stream, into the stripped aniline and nitrobenzene being provided to said aniline cleaning apparatus, and an effluent which is an aqueous waste stream being fit for treatment in a biological waste stream treating unit.

The stream of stripped aniline and nitrobenzene comprises also water. Recycling of water together with the stripped aniline and nitrobenzene, to the aniline cleaning apparatus, optionally via the reactor for conversion of nitrobenzene into aniline, is not a major issue. This is because the nitrobenzene stream already comprises water and the conversion of nitrobenzene into aniline generates water as well.

The stripping column may include a reboiler or use live steam injection. Heating of the reboiler in particular, and the stripping column in general, may be obtained by using high or low pressure steam which partially or in total is generated by one or more of the nitrobenzene production unit, the aniline production unit and the DADPM production unit.

The stripping column may work at a pressure substantially equal to atmospheric, i.e. in a range of $0.95*10^5$ Pa absolute (0.95 bara) to $1.2*10^5$ Pa absolute (1.2 bara). In such conditions, the temperature of the stripping column is typically set in a range of 98 deg C. to 110 deg C. The temperatures quoted are at the bottom of the column and are dependent upon the strength of brine leaving in the effluent.

As an alternative, the stripping column may be operated using pressures above atmospheric pressure, optionally under a pressure of $3*10^5$ Pa absolute (3 bara) to $11*10^5$ Pa absolute (11 bara) e.g. at $7*10^5$ Pa absolute (7 bara). The temperature of the stripping column may be set in a range 134 deg C. to 190 deg C., e.g. in the range of 160 deg C. to 170 deg C.

The stripped aniline and nitrobenzene is accompanied with water when leaving the stripping column in a vapor phase. The vapor comprising aniline, nitrobenzene and water vapor coming from the stripping column, may be condensed and cooled. This condensing may be done in a methanol fractionator column which may be present in the DADPM production unit.

The condensate may thereafter be separated in an aqueous phase, comprising water and some of the stripped nitrobenzene and aniline, and an organic phase, comprising the stripped aniline and nitrobenzene, and some water. This separation may be obtained in a phase separation apparatus, where the aqueous phase is the light phase, the organic phase is the heavy phase.

Preferably only this organic phase is provided back to the aniline cleaning apparatus, whereas optionally the aqueous phase is recycled to the stripping column as a further feed, next to the three waste streams.

According to some embodiments of the present invention, the chemical installation further may comprise a condenser for condensing the stripped aniline and nitrobenzene, accompanied with water, and a separator, optionally a phase separator, for separating the condensed aniline, nitrobenzene and water in an aqueous phase, comprising water and some of the stripped nitrobenzene and aniline, and an organic phase comprising the stripped aniline, nitrobenzene and some water.

According to some embodiments of the present invention, the chemical installation may comprise recycling means for recycling the aqueous phase in to the stripping column.

Some of the condensate may be returned to the top of the stripping column, where it is used to knock down droplets and optionally solids in the vapor phase, which phase is to leave the stripping column. This knocking down can be done using preferably a trayed section, though also a structured packing section might be used.

Optionally some heat may be taken from the stripped aniline and nitrobenzene, in its vapor phase together with water after the stripping column. This heat may be recuperated as steam, optionally as low to medium pressure steam, i.e. from just above atmospheric pressure to $9*10^5$ Pa absolute (9 bara).

The nitrobenzene production unit provides an aqueous waste stream comprising nitrobenzene (the first waste stream), which may comprise nitrites. These components, when brought into contact with an amine in an acidic environment, may form tar, which could cause the stripping column to become fouled or even blocked. It was found that by feeding the waste streams to the stripping column separately, the risk of tar being formed by contacting nitrites from the first waste stream with the aniline is reduced or may even be avoided.

According to some embodiments of the present invention, the stripping column may have n theoretical trays A1 to An, A1 being the top tray, An being the bottom tray. The second waste stream may be introduced in the stripping column at theoretical tray Ax, x being greater or equal to 1. The first waste stream may be introduced in the stripping column at a theoretical tray A[y], wherein [y] is the integer of y and y fulfills the equation $0.5*(n+1)+0.5*x<y<0.85*(n+1)+0.15*x$.

More preferred, y fulfills the equation $0.57*(n+1)+0.43*x<y<0.85*(n+1)+0.15*x$. It is even more preferred that y fulfills the equation $0.7*(n+1)+0.3*x<y<0.75*(n+1)+0.25*x$.

In practice, this means that the waste water comprising nitrobenzene is fed to the stripper at a significantly large distance under the entry of the waste water comprising aniline.

Nitrobenzene can be stripped from water more easy as compared to aniline. Feeding the nitrobenzene comprising waste stream well under the aniline comprising waste stream or streams as explained above, also gave the advantage that the aniline is not further diluted by the water present in the nitrobenzene comprising waste stream, resulting in an efficient stripping of the aniline, whereas the further dilution of the nitrobenzene with the water from the aniline comprising waste streams fed at a position above the nitrobenzene comprising waste stream feed, does not significantly decrease the stripping efficiency of the nitrobenzene from the aqueous stream.

By applying this distinct feeding of the two waste streams, the overall amount of organic components being aniline and nitrobenzene in the resulting stream for the bio-treatment can be reduced if all other factors remain constant.

Additionally it was found that handling the two aqueous streams in a common stripper, with the streams' feed positions to the column optimised as explained above, allows a more economical use of energy necessary to run the stripping columns. Keeping the amount of organics per volume bio-treatable waste stream in the range of 200 to 500 ppb, using the same amount of packing material, and treating equal volumes of first and second aqueous streams in all cases, it was found that, comparing the steam (hence energy) consumption of one stripping column (using all packing material) treating both first and second aqueous streams simultaneously, may be about 15% less than the steam necessary to run two stripping columns, one for stripping the aniline from a same volume of the second aqueous stream, and the other for stripping the nitrobenzene from the same volume of first aqueous stream, the packing material being divided over the two stripping columns.

Similarly, keeping the amount of organics per volume bio-treatable waste stream in the range of 200 to 500 ppb, using an equal amount of steam, and treating equal volumes of first and second aqueous streams in all cases, it was found that, comparing the packing material of one stripping column treating both first and second aqueous streams simultaneously, may be about 16% less than the total height of packing material present in two stripping columns, one for stripping the aniline from a same volume of the second aqueous stream, and the other for stripping the nitrobenzene from the same volume of first aqueous stream. Hence a reduction of either installation cost and height (volume) of packing material, or a reduction of energy consumption of about 15% may be obtained when handling the two aqueous streams in a common stripper.

Providing the two aqueous streams at different positions to the stripping column as described above, has the advantage that the amount of packing material or theoretical trays in the stripping column can be kept at tolerable level, as compared to using combined feeds of the two aqueous streams, which, for the same purity of effluent and same energy consumption, would cause the packing height or number of theoretical trays to be multiplied by a factor greater than 4.

In order to further reduce the risk on forming tar by reaction of nitrites with aniline in the stripping column, the first waste stream comprising nitrobenzene, may be neutralized by adding a basic component, preferably caustic soda.

According to a second aspect of the present invention, an installation according to the first aspect of the present invention may be used in the production process for producing DADPM.

According to a second aspect of the present invention, a method for producing DADPM is provided, the method comprising
converting benzene into nitrobenzene thereby providing a nitrobenzene stream and a first aqueous waste stream comprising nitrobenzene;
converting the nitrobenzene from said nitrobenzene stream into aniline, thereby providing an aniline stream and a first part of a second aqueous waste stream comprising aniline;
removing nitrobenzene from the aniline prior to converting the aniline from said aniline stream into DADPM;
converting the aniline from the aniline stream into DADPM thereby providing a second part of said second aqueous waste stream comprising aniline;
stripping aniline and nitrobenzene from the first and second aqueous waste stream by means of a stripping column;
providing the stripped aniline and nitrobenzene to an aniline cleaning apparatus or to said nitrobenzene stream.

Preferably the stripped aniline and nitrobenzene may be provided to the aniline cleaning apparatus.

According to some embodiments of the present invention, the aniline production unit may comprise a reactor for converting the nitrobenzene into aniline, said converting the nitrobenzene from the nitrobenzene stream into aniline comprises provided the stripped aniline and nitrobenzene to the reactor for converting the nitrobenzene into aniline;
converting nitrobenzene into aniline in a reactor; and
removing nitrobenzene from the provided aniline using an aniline cleaning apparatus.

According to some embodiments of the present invention, the aniline production unit may comprise a reactor for converting the nitrobenzene into aniline, said converting the nitrobenzene from the nitrobenzene stream into aniline comprises converting nitrobenzene into aniline in the reactor;
providing the stripped aniline and nitrobenzene to the aniline obtained as reactor effluent; and
removing nitrobenzene from the aniline using an aniline cleaning apparatus.

According to some embodiments of the present invention, the stripping column may have n theoretical trays A1 to An, A1 being the top tray, An being the bottom tray, the second waste stream being introduced in the stripping column at theoretical tray Ax, x being greater or equal to 1, the first waste stream being introduced in the stripping column at a theoretical tray A[y], wherein [y] is the integer of y and y fulfills the equation $0.5*(n+1)+0.5*x<y<0.85*(n+1)+0.15*x$.

According to some embodiments of the present invention, the stripping column may provide the stripped aniline and nitrobenzene, accompanied with water as a vapor, the method further comprising condensing the stripped aniline and nitrobenzene, accompanied with water and separating the condensed aniline, nitrobenzene and water in an aqueous phase, comprising water and some of the stripped nitrobenzene and aniline, and an organic phase comprising the stripped aniline, nitrobenzene and some water.

According to some embodiments of the present invention, the aqueous phase may be recycled to the stripping column as a further feed, next to the first and second waste streams.

The independent and dependent claims set out particular and preferred features of the invention. Features from the dependent claims may be combined with features of the independent or other dependent claims as appropriate.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

The same reference signs refer to the same, similar or analogous elements in the different figures.

The present invention will be described with respect to particular embodiments.

It is to be noticed that the term "comprising", used in the claims, should not be interpreted as being restricted to the means listed thereafter; it does not exclude other elements or steps. It is thus to be interpreted as specifying the presence of the stated features, steps or components as referred to, but does not preclude the presence or addition of one or more other features, steps or components, or groups thereof. Thus, the scope of the expression "a device comprising means A and B" should not be limited to devices consisting only of components A and B. It means that with respect to the present invention, the only relevant components of the device are A and B.

Throughout this specification, references to "one embodiment" or "an embodiment" are made. Such references indicate that a particular feature, described in relation to the embodiment, is included in at least one embodiment of the present invention. Thus, appearances of the phrases "in one embodiment" or "in an embodiment" in various places throughout this specification are not necessarily all referring to the same embodiment, though they could. Furthermore, the particular features or characteristics may be combined in any suitable manner in one or more embodiments, as would be apparent to one of ordinary skill in the art.

The following terms are provided solely to aid in the understanding of the invention.

The term DADPM refers to "methylene-bridged polyphenyl polyamines", including diaminodiphenylmethane isomers, and higher homologues thereof or higher polymers thereof.

The term "bara" refers to "bar absolute" and indicates the absolute pressure.

Unless otherwise indicated, "% w" refers to the weight percentage of the component, expressed in reference to the total weight of the composition in which it is present.

Figure 1:
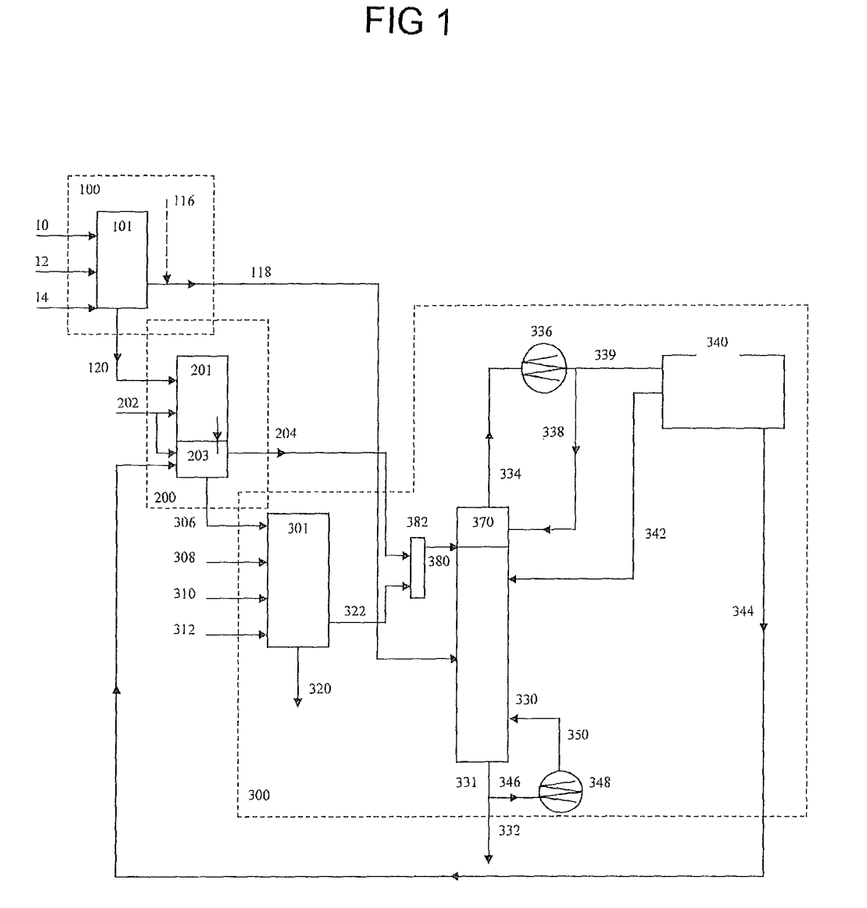
FIG. 1 is a schematic view of chemical installation according to the present invention.
Figure 2:
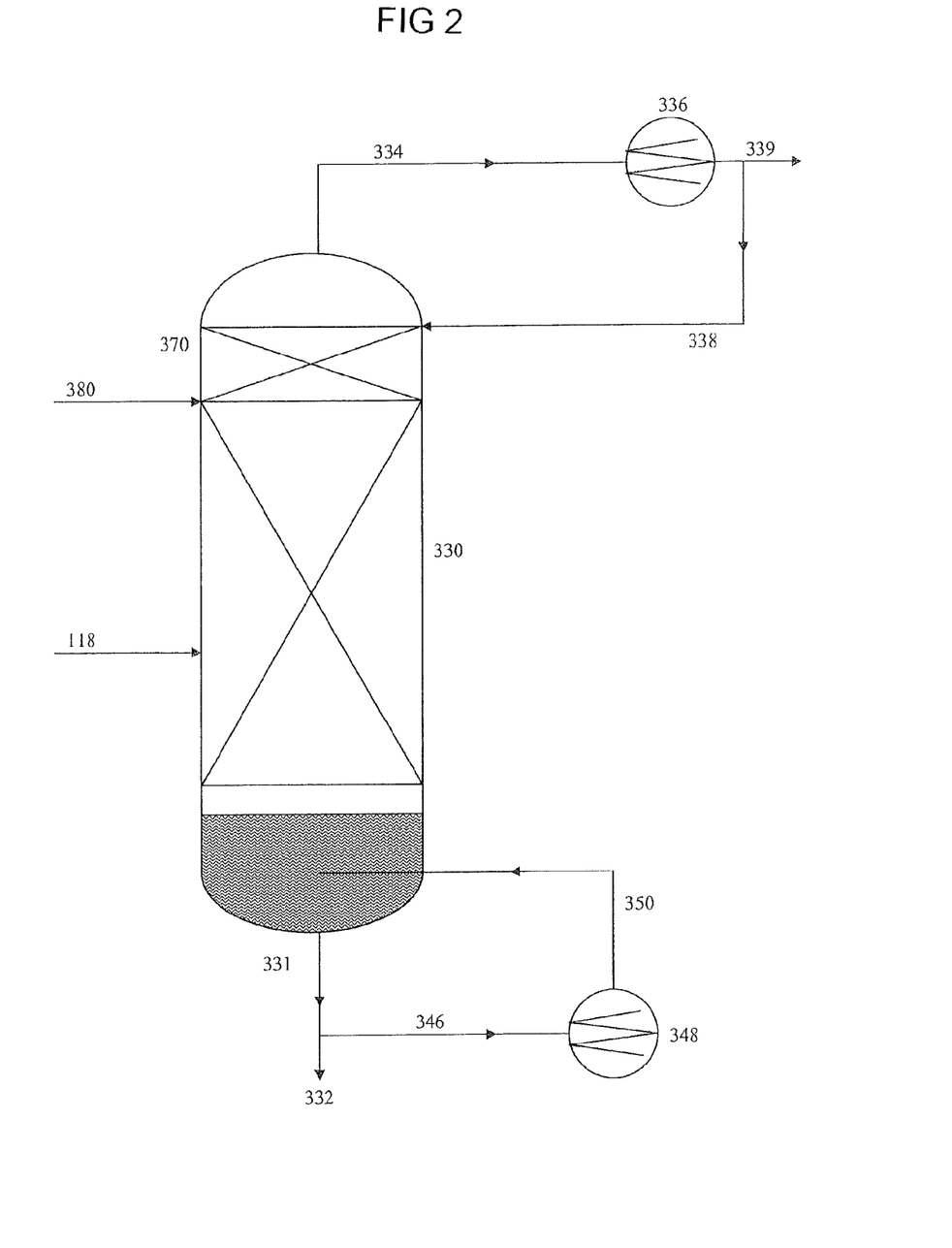
FIG. 2 is a schematic view of the stripping column as used in a method and installation according to the present invention.

In FIG. 1, a schematic view of chemical installation according to the present invention is shown. FIG. 2 is a schematic view of the stripping column 330.

For the sake of easiness, in FIGS. 1 and 2, the following reference signs are used to indicate product streams as set out in table 1.

TABLE 1

| | |
|---|---|
| 110 | Benzene |
| 112 | Sulphuric acid |
| 114 | Nitric acid |
| 116 | Caustic soda |
| 118 | First aqueous waste stream |
| 120 | Nitrobenzene |
| 202 | Hydrogen |
| 204 | First part of the second aqueous waste stream |
| 306 | Aniline |
| 308 | Formaldehyde |
| 310 | Hydrochloric acid |
| 312 | Caustic soda |
| 320 | DADPM |
| 322 | second part of second aqueous waste stream |
| 331 | Aqueous waste stream for bio-treatment |
| 332 | Aqueous waste stream for bio-treatment towards biological treatment |
| 334 | Stripped aniline, nitrobenzene and water vapor to condenser |
| 338 | Condensed stripped aniline, nitrobenzene and water return to stripping column |
| 339 | Condensed stripped aniline, nitrobenzene and water to phase separator |
| 342 | Aqueous phase separator return to stripping column |
| 344 | Organic phase comprising aniline and nitrobenzene return to aniline cleaning apparatus |
| 346 | Aqueous waste stream return to heater |
| 350 | Aqueous waste stream return to stripping column |
| 380 | second aqueous waste stream |

A chemical installation according to the present invention comprises a nitrobenzene production unit 100 for converting benzene 110 into nitrobenzene thereby providing a nitrobenzene stream 120 and a first aqueous waste stream 118 comprising some nitrobenzene.

Relatively pure benzene is provided to a suitable reactor, where it reacts with nitric acid 114 in the presence of sulphuric acid 112. The nitric acid, and to a less extent the sulphuric acid is diluted with water.

The nitrobenzene obtained is relatively pure (more than 99 wt %). The first waste stream is an acid aqueous waste stream comprising some nitrobenzene. Optionally the waste stream was neutralized using caustic soda 116. After neutralization, the first waste stream 118 comprises, next to the water and next to the salts resulting from the neutralization of the remaining acids by caustic soda, some nitrobenzene (typically less than 0,5 wt %), some nitrates and some nitrite.

A chemical installation according to the present invention comprises an aniline production unit 200 for converting the nitrobenzene from the nitrobenzene stream 120 into aniline, thereby providing an aniline stream 306 and an aqueous waste stream comprising aniline, forming a first part 204 of the second aqueous waste stream 380 comprising aniline.

The aniline production unit may comprise a reactor 201 for converting the bulk amount of the nitrobenzene into aniline using hydrogen from the hydrogen stream 202. In a second reactor, i.e. the aniline cleaning apparatus 203, the effluent of the reactor 201 is further treated with an excess of hydrogen 202 for completing the conversion of nitrobenzene into aniline.

After this aniline cleaning apparatus 203, the aniline is separated from the water, typically using a phase separator thereby providing an aqueous phase which is a part, i.e. the first part 204 of the second aqueous waste stream 380 comprising water and aniline, and an aniline stream 306. As an alternative, the aniline is separated from the water prior to the aniline cleaning apparatus, also providing an aqueous stream suitable to be a first part of the second aqueous waste stream comprising water and aniline.

The aniline obtained is relatively pure (97 wt % to 99 wt %). The first part 204 of the second waste stream 380 is an aqueous waste stream comprising aniline and may comprise 4 wt % to 5 wt % aniline, e.g. 4,04 wt %.

A chemical installation according to the present invention further comprises a DADPM production unit 300 for converting the aniline from the aniline stream 306 into DADPM thereby providing a DADPM stream 320 and a second part 322 of the second aqueous waste stream 380 comprising aniline.

The aniline stream 306 is reacted with formaldehyde 308, provided as formalin comprising about 44 wt % formaldehyde, in presence of an acid catalyst, being hydrochloric acid 310. After having converted the aniline into DADPM, the resulting liquid is neutralized and separated via phase separation into an organic DADPM stream and a salty, aqueous phase. This salty, aqueous phase is then washed with aniline to remove remaining DADPM and again separated into an organic phase (aniline) and an aqueous, salty phase or brine, which comprises water and some aniline, being a second part 322 of the second aqueous waste stream 380. It is understood that the reactor part 301 of this DADPM production unit 300 may comprise various reactors and apparatuses one coupled to the other.

The second part 322 of the second waste stream 380 is an aqueous waste stream mainly comprising aniline (about 1,71 wt %), water (81,08 wt %) and sodium chloride (16,55 wt %).

The two parts of the second waste stream 380 are mixed together in a feed vessel 382 and fed together (via some interchangers) to just below the rectification section 370.

The DADPM production unit 300 of the chemical installation further comprises a stripping column 330 for stripping aniline from an aqueous stream.

As shown in general in FIG. 1, the first and second aqueous waste stream (118, 380) are provided to this stripping column 330.

The stripping column 330 strips aniline and nitrobenzene from these first and second aqueous waste stream and provides aniline and nitrobenzene, accompanied by water as a vapor at the top of the stripping column 330. At the bottom of the stripping column 330, a liquid being bio-treatable water 331 is obtained. A first part 346 of this bio-treatable water 331 is heated in a heat exchanger 348.

The heated water 350 returns to the stripping column 330 at the bottom side and causes water vapor to rise to the top part of the stripping column 330, thereby stripping the nitrobenzene and thereafter the aniline from the incoming waste water streams 118 and 380. As an example, a thermosyphon reboiler may be used. The outlet of the exchanger is a mixed stream, with around 20% vapour. This mixed stream is returned to the sump of the column (above the liquid level), where the vapour and liquid effectively separate. The bio-treatable water stream 332 further comprises the salts which were present in the incoming waste streams, and is forwarded to a biological waste water treatment unit (not shown).

The stripped aniline and nitrobenzene, together with the water, is taken of at the top of the stripping column 330 as vapor stream 334. The vapor 334 is cooled and condensed in cooler 336, where some of the heat might be recuperated as steam being formed in this cooler 336.

A first part 338 of the condensate is returned to the top of the stripping column, where it is used to knock down droplets and optional solids which might be entrained with the vapor in a short rectification section 370. This short rectification section 370 may be a trayed section.

The second, major part 339 of the condensed stripped aniline and nitrobenzene together with water is provided to a phase separator 340. Optionally, the condensed stripped aniline and nitrobenzene together with water is provided to a Methanol Fractionator, where it flashes and the vapours again condense. Light components can be removed as such. The bottom stream from this Methanol Fractionator is passed to a phase separator, where an aqueous phase comprising the water and some of the stripped aniline and nitrobenzene is provided.

This aqueous phase 342 is returned to the stripping column 330 again, and comprises typically about 95,86 wt % water, about 3,78 wt % aniline and further methanol and traces at ppm level of other components.

The stripping column 330, including the rectification section 370, has 30 theoretical trays, two of which are used as rectification section. The aqueous stream 380 comprising aniline is fed in the stripping column 330 at the height of the third tray. The first and second tray, located above this feed, hence function as rectification section 370.

The aqueous waste stream 118 comprising nitrobenzene is fed into the stripping column at the height of the twenty-second theoretical tray. As is clear from the table 2, feeding the aqueous stream comprising nitrobenzene at different positions, and maintaining all other operational parameters of the stripping column equal, has a tremendous influence on the organic content of the aqueous waste stream 331 for bio-treatment. For the column 330 with aqueous, aniline comprising feed at tray 3, and using 30 trays of which 2 are located above the aqueous, aniline comprising feed, it is preferred to feed the aqueous, nitrobenzene comprising feed 380 at the height between the eighteenth and the twenty-fifth tray, most preferably at tray twenty-two or twenty three. Doing so, the amount of organic components in the effluent stream can be kept at a level less than 3000 ppb.

TABLE 2

| Number of theoretical trays in column | Feed position | | Effluent composition | | |
|---|---|---|---|---|---|
| | Aqueous feed comprising aniline fed at tray | Aqueous feed comprising NITRO-BENZENE fed at tray | Aniline (ppb) | NITRO-BENZENE (ppb) | Total (Ppb) |
| 30 | 3 | 3 | 1297890 | 1.39E−05 | 1297890 |
| 30 | 3 | 13 | 15119 | 0.030252 | 15119 |
| 30 | 3 | 14 | 10510 | 0.07657 | 10510 |
| 30 | 3 | 15 | 7323 | 0.19432 | 7323 |
| 30 | 3 | 16 | 5120 | 0.49401 | 5121 |
| 30 | 3 | 17 | 3592 | 1.258 | 3593 |
| 30 | 3 | 18 | 2528 | 3.2049 | 2531 |
| 30 | 3 | 19 | 1786 | 8.171 | 1794 |
| 30 | 3 | 20 | 1267 | 20.844 | 1288 |
| 30 | 3 | 21 | 903 | 53.197 | 956 |
| 30 | 3 | 22 | 647 | 135.83 | 783 |
| 30 | 3 | 23 | 466 | 347.37 | 814 |
| 30 | 3 | 24 | 338 | 887.24 | 1226 |
| 30 | 3 | 25 | 248 | 2267.2 | 2515 |
| 30 | 3 | 26 | 184 | 5794.4 | 5978 |
| 30 | 3 | 27 | 138 | 14805 | 14943 |
| 30 | 3 | 28 | 105 | 37779 | 37884 |
| 30 | 3 | 29 | 82 | 96111 | 96193 |
| 30 | 3 | 30 | 65 | 242620 | 242685 |

The organic (more heavy) phase of the phase separator 340 comprises the major part of the stripped aniline and nitrobenzene, together with a minor amount of water. About 85 wt % to 95 wt %, such as 92,6 wt %, of the aniline fed to the phase separator leaves in the organic stream. The other part of the aniline part returns to the stripper with the aqueous stream 342. Similarly, 90 wt % to 99.9 wt % of the nitrobenzene passes with the organic stream, the other part returns to the stripper.

This organic phase of the phase separator 340 is returned as stream 344 to the aniline cleaning apparatus 203, where it is, together with the effluent of the reactor 201, further hydrogenated with an excess of hydrogen 202 for completing the conversion of nitrobenzene into aniline, and this optionally after the aniline being separated from the water by means of a phase separator. It is clear that the aniline which comes with the stream 344 becomes part of the aniline stream.

In an alternative setup, the organic phase of the phase separator 340 is returned as stream 344 to the aniline reactor 201, where it is hydrogenated with hydrogen 202. The nitrobenzene present in the stream 344 is converted, at least partially, into aniline, and further provided to the aniline cleaning apparatus 203 for completing the conversion of nitrobenzene into aniline.

It is to be understood that although preferred embodiments and/or materials have been discussed for providing embodiments according to the present invention, various modifications or changes may be made without departing from the scope and spirit of this invention.

The invention claimed is:

1. A method for producing diaminodiphenylmethane (DADPM), the method comprises:
  converting benzene into nitrobenzene thereby providing a nitrobenzene stream and a first aqueous waste stream comprising nitrobenzene;
  converting said nitrobenzene from said nitrobenzene stream into aniline, thereby providing an aniline stream and a first part of a second aqueous waste stream comprising aniline;
  removing nitrobenzene from said aniline prior to converting said aniline from said aniline stream into DADPM;
  converting said aniline from said aniline stream into DADPM thereby providing a second part of said second aqueous waste stream comprising aniline;
  stripping aniline and nitrobenzene from said first and second aqueous waste stream by means of a stripping column;
  providing the stripped aniline and nitrobenzene to said aniline cleaning apparatus or to said nitrobenzene stream; and
  wherein said stripping column has n theoretical trays A1 to An, A1 being the top tray, An being the bottom tray, said second waste stream being introduced in the stripping column at theoretical tray Ax, x being greater or equal to 1, said first waste stream being introduced in the stripping column at a theoretical tray A[y], wherein [y] is the integer of y and y fulfills the equation $0.5*(n+1)+0.5*x < y < 0.85*(n+1)+0.15*x$.

2. The method for producing DADPM according to claim 1, wherein the said aniline production unit comprises a reactor for converting said nitrobenzene into aniline, the converting said nitrobenzene from said nitrobenzene stream into aniline comprises
  providing said stripped aniline and nitrobenzene to said reactor for converting said nitrobenzene into aniline;
  converting nitrobenzene into aniline in a reactor; and
  removing nitrobenzene from the provided aniline using an aniline cleaning apparatus.

3. The method for producing DADPM according to claim 1, wherein the said aniline production unit comprises a reactor for converting said nitrobenzene into aniline, the converting said nitrobenzene from said nitrobenzene stream into aniline comprises
  converting nitrobenzene into aniline in said reactor;
  providing said stripped aniline and nitrobenzene to said aniline obtained as reactor effluent; and
  removing nitrobenzene from the aniline using an aniline cleaning apparatus.

4. The method for producing DADPM according to claim 1, wherein said stripping column provides the stripped aniline and nitrobenzene, accompanied with water as a vapor, the method further comprising condensing said stripped aniline and nitrobenzene, accompanied with water and separating said condensed aniline, nitrobenzene and water in an aqueous phase, comprising water and some of the stripped nitrobenzene and aniline, and an organic phase comprising the stripped aniline, nitrobenzene and some water.

5. The method according to claim 4, wherein said aqueous phase is recycled to the stripping column as a further feed, next to the first and second waste streams.

\* \* \* \* \*